(12) United States Patent
Fukui et al.

(10) Patent No.: US 7,365,840 B2
(45) Date of Patent: Apr. 29, 2008

(54) INFORMATION PRESENTING SUBSTANCE-CONTAINING MATERIAL, AND IDENTIFICATION METHOD, IDENTIFICATION SYSTEM AND DEVICE THEREFOR

(75) Inventors: Shinya Fukui, 3-20-1, Midorigaoka, Toyonaka-shi, Osaka 560-0002 (JP); Yoshihito Miyako, Sakai (JP); Yasuo Kanematsu, Suita (JP); Hiromasa Hanzawa, Toyonaka (JP)

(73) Assignee: Shinya Fukui, Toyonaka-Shi (JP)

( * ) Notice: Subject to any disclaimer, the term of this patent is extended or adjusted under 35 U.S.C. 154(b) by 359 days.

(21) Appl. No.: 10/499,652

(22) PCT Filed: Dec. 26, 2002

(86) PCT No.: PCT/JP02/13705

§ 371 (c)(1),
(2), (4) Date: Nov. 23, 2004

(87) PCT Pub. No.: WO03/058549

PCT Pub. Date: Jul. 17, 2003

(65) Prior Publication Data

US 2005/0083720 A1 Apr. 21, 2005

(30) Foreign Application Priority Data

Dec. 28, 2001 (JP) .............................. 2001-400119

(51) Int. Cl.
*G06K 9/74* (2006.01)
*G01J 3/00* (2006.01)
*G01J 3/30* (2006.01)

(52) U.S. Cl. ........................ 356/300; 356/71; 356/317

(58) Field of Classification Search ................. 356/71; 422/82.07, 82.08; 436/56
See application file for complete search history.

(56) References Cited

U.S. PATENT DOCUMENTS

| | | | | |
|---|---|---|---|---|
| 4,018,635 | A * | 4/1977 | Ryan et al. | 149/2 |
| 4,755,469 | A * | 7/1988 | Showalter et al. | 436/27 |
| 5,279,967 | A * | 1/1994 | Bode | 436/56 |
| 6,617,583 | B1 * | 9/2003 | Bawendi et al. | 250/370.01 |
| 6,692,031 | B2 * | 2/2004 | McGrew | 283/93 |
| 7,112,445 | B1 * | 9/2006 | Welle | 436/56 |

FOREIGN PATENT DOCUMENTS

| | | |
|---|---|---|
| JP | 8-269370 | 10/1996 |
| JP | 10-90182 | 4/1998 |
| JP | 10-283445 | 10/1998 |
| JP | 2001-356689 | 12/2001 |

* cited by examiner

*Primary Examiner*—Gregory J. Toatley, Jr.
*Assistant Examiner*—Jonathan Skovholt
(74) *Attorney, Agent, or Firm*—Kratz, Quintos & Hanson, LLP

(57) ABSTRACT

A material includes various encrypted information such as product type information, product history information and authentication judging information by using an information presenting substance exhibiting line spectrums and associated with certain encrypted information corresponding to the line spectrums. Line spectrum of the information presenting substance is detected by irradiating electromagnetic waves to the material. Since the line spectrum is narrow in half-width and strong in light emitting intensity, the distinctiveness is high and therefore the encrypted information included in the material can be specified assuredly, enabling the simple and assured identification of the material.

16 Claims, 14 Drawing Sheets

INFORMATION PRESENTING SUBSTANCE-CONTAINING MATERIAL, AND IDENTIFICATION METHOD, IDENTIFICATION SYSTEM AND DEVICE THEREFOR

TECHNICAL FIELD

The present invention relates to information presenting substance-containing material capable of easily and assuredly performing processing operations such as a separation of waste materials depending on categories, a tracking survey of production history of a certain product and checking of authenticity of a certain product. It also relates to an identification method, an identification system and an identification device for performing the aforementioned processing operations.

BACKGROUND ART

Conventionally, an identification of material such as plastics has been performed by any one or plural combinations of physical analysis for analyzing gravity, hardness, melting point, dielectric constant, color tone, etc. of the material and chemical analysis for analyzing infrared spectrum or heat of the material.

In the case of physical analysis for identifying the material, however, there are drawbacks that generally it is required to adjust and/or destroy the material and that it takes a long time to complete the analysis. On the other hand, in the case of chemical analysis for identifying the material, in the infrared spectrum analysis there are drawbacks that accurate analysis cannot be expected when the surface is contaminated, and in thermal analysis there are drawbacks that it is required to melt the material. Furthermore, although both the analyses, i.e., physical analysis and chemical analysis, can identify the type of material, it is difficult to identify the production history or manufacturer of the material.

A method capable of solving the aforementioned drawbacks has been known (e.g., Japanese Unexamined Laid-open Patent Publication No. H8-269370). This method includes the step of: adding one or more elements to the material to be identified; irradiating the material with an X-ray; detecting the spectrum radiated from the element(s); and identifying the material based on the detected spectrum.

In general, however, the spectrum emitted from the aforementioned element(s) or compositions is wide in half-width $\Delta \lambda$ (i.e., bandwidth at the half value of the peak light emitting intensity). Therefore, in cases where the spectrum overlaps with a spectrum having characteristics similar to the wavelength $\lambda$, it is difficult to discriminate them, which makes it difficult to identify the encrypted information included in the material.

The present invention was made in view of the aforementioned problems, and aims to provide information presenting substance-containing material excellent in spectrum identification and capable of assuredly specifying encrypted information included in the material and therefore capable of easily and assuredly identifying the material. It also aims to provide the method, the system and the device for identifying the material.

More specifically, the present invention aims to provide information presenting substance-containing material including various encrypted information such as not only the material type information but also the production history information and the authentication judging information and enabling easy and assured processing operations such as a separation of waste materials depending on categories, a tracking survey of production history of a certain product, and checking of authenticity of a certain product. It also aims to provide the identification method, the identification system and the identification device for performing the aforementioned processing operations.

DISCLOSURE OF INVENTION

An information presenting substance-containing material according to the present invention contains an information presenting substance, wherein the information present substance is a compound including one or more ions selected from the group consisting of a transition element ion having an incomplete 3d shell, a transition element ion having an incomplete 4d shell, a transition element ion having an incomplete 5d shell and a rare-earth element ion and therefore exhibiting one or plural line spectrums and, and wherein the information presenting substance is associated with specific encrypted information corresponding to the one or plural line spectrums.

The encrypted information can be information regarding the material itself such as the material type information, the product history information and the manufacture, or can be information regarding the product in which the material is used.

According to the above, by mixing the information presenting substance into the material to be identified, the material can have various encrypted information such as the type information, the product history information and the authentication information.

The line spectrum to be used for identifying the encrypted information is narrow in half-width and strong in light emitting intensity. Therefore, the identifiability is high, enabling the encrypted information included in the material to be simply and assuredly identified, which results in an easy and assured identification of the material.

Furthermore, even if the same type and amount of the aforementioned element ion is used, the information presenting substance exhibits different line spectrum depending on the type of the compound in which the element ion is included. Accordingly, by combining the element ion and the compound, a large variety of line spectrums can be created, enabling various encrypted information to be included in the material.

Furthermore, since the information presenting substance seldom exists in general material, a desired line spectrum can be detected even in an environment existing noises generated under various conditions.

Plural types of the information presenting substances can be included in the material.

In this case, since the material exhibits a plurality of line spectrums due to the combination of plural types of information presenting substances, various encrypted information can be easily included in the material.

Furthermore, it can be constituted that the encrypted information is associated with the plural line spectrums and represented by plural digit numeric data, wherein each digit of the numeric data corresponds to a wavelength of each line spectrum and a value of each digit corresponds to light emitting intensity of each line spectrum.

In this case, the line spectrum group consisting of a plurality of line spectrums can be used as a bar-code, enabling plural digit numeric encrypted information to be included in the material.

It is preferable that the information presenting substance exhibits at least one line spectrum within a wavelength region covering from ultraviolet light to infrared light.

In this case, since the line spectrums in the wavelength region from ultraviolet light to infrared light can be detected with a small or simple device, the material can be easily identified at a desired location without paying special safety attention required when using a large detecting device.

Furthermore, in the case where the compound as the information presenting substance is an organic compound, the information presenting substance becomes excellent in thermal durability and strong against ultraviolet light. In the case where the compound is an organic compound, the information presenting substance becomes readily soluble in organic materials and increases in light emitting intensity of the line spectrums. In the case where the compound is an organic and inorganic complex compound, the information presenting substance can have both the characteristics of the non-organic compound and the organic compound.

In the case where the information presenting substance is a crystal, the information presenting substance can stably exhibit line spectrums.

In the case where the information presenting substance is an amorphous substance, since the line spectrums become complicated, it becomes difficult for a third party to reproduce maliciously, resulting in further enhanced security of the encrypted information included in the material.

In the case where the information presenting substance is a complex, since the complex has dye-like characteristics, the information presenting substance becomes readily soluble in organic materials and increases in light emitting intensity of the line spectrums.

Furthermore, in the case where the information presenting substance is a semiconductor, the information presenting substance increases in light emitting intensity of line spectrums.

Furthermore, it is preferable that the material is plastic.

In this case, it is possible to cause the information presenting substance to be easily included in the plastic material at the time of molding the plastic material. In addition, due to the thermoplastic characteristics of the plastic materials, it is impossible to cause the information presenting substance to be included in plastic material unless the state of the material is changed by heat after the molding. Therefore, malicious addition of encrypted information by a third party can be prevented.

A product according to the present invention uses the aforementioned information presenting substance-containing material.

In this case, it is possible to cause the information presenting substance to be easily included in the plastic material at the time of molding the plastic material. In addition, since it is impossible to cause the information presenting substance to be included in plastic material after the molding, malicious addition of encrypted information by a third party can be prevented.

In a method for identifying information presenting substance-containing material according to the present invention, the information presenting substance is a compound including one or more ions selected from the group consisting of a transition element ion having an incomplete 3d shell, a transition element ion having an incomplete 4d shell, a transition element ion having an incomplete 5d shell and a rare-earth element ion and therefore giving one or plural line spectrums, and the information presenting substance is associated with specific encrypted information corresponding to the one or plural line spectrums, the method, includes the steps of: storing the line spectrums and the encrypted information in an associated manner in a storing means; detecting the line spectrums of the information presenting substance by irradiating electromagnetic waves within a certain wavelength region against the information presenting substance-containing material or a product using the material; and identifying the information presenting substance-containing material by specifying corresponding encrypted information based on the detected line spectrums.

In this case, the line spectrum to be used for identifying the encrypted information is narrow in half-width and strong in light emitting intensity. Therefore, the identifiability is high, enabling the encrypted information included in the material to be simply and assuredly specified, which results in an easy and assured identification of the material.

An information presenting substance-containing material identification system according to the present invention is an identification system for identifying the information presenting substance-containing material, wherein the information presenting substance is a compound including one or more ions selected from the group consisting of a transition element ion having an incomplete 3d shell, a transition element ion having an incomplete 4d shell, a transition element ion having an incomplete 5d shell and a rare-earth element ion and therefore exhibiting one or plural line spectrums, and the information presenting substance is associated with specific encrypted information corresponding to the one or plural line spectrums, the system includes: a storing means which stores the line spectrums and the encrypted information in an associated manner in a storing means; a detecting means which detects the line spectrums of the information presenting substance by irradiating electromagnetic waves within a certain wavelength region against the information presenting substance-containing material or a product using the material; and an identifying means which identifies the material by specifying corresponding encrypted information from the storing means based on the line spectrums detected by the detecting means.

In this case, the line spectrum to be used for identifying the encrypted information is narrow in half-width and strong in light emitting intensity. Therefore, the identifiability is high, enabling the encrypted information included in the material to be simply and assuredly specified, which results in an easy and assured identification of the material.

Furthermore, an identification device according to the present invention is an identification device for use in the aforementioned information presenting substance-containing material identification system, wherein the device includes: a storing means which stores the line spectrums and the encrypted information in an associated manner; and an identifying means which identifies the material by specifying corresponding encrypted information from the storing means based on the line spectrums detected by a detecting means for detecting the line spectrums of the information presenting substance by irradiating electromagnetic waves within a certain wavelength region against the information presenting substance-containing material or a product using the material.

With this system, it becomes possible to easily and assuredly realize the identification system by disposing the identification device at a predetermined position and connecting to a detecting means for detecting the line spectrums in a communicated manner.

BEST MODE FOR CARRYING OUT THE INVENTION

[Information Presenting Substance-Containing Material]

Figure 1A:
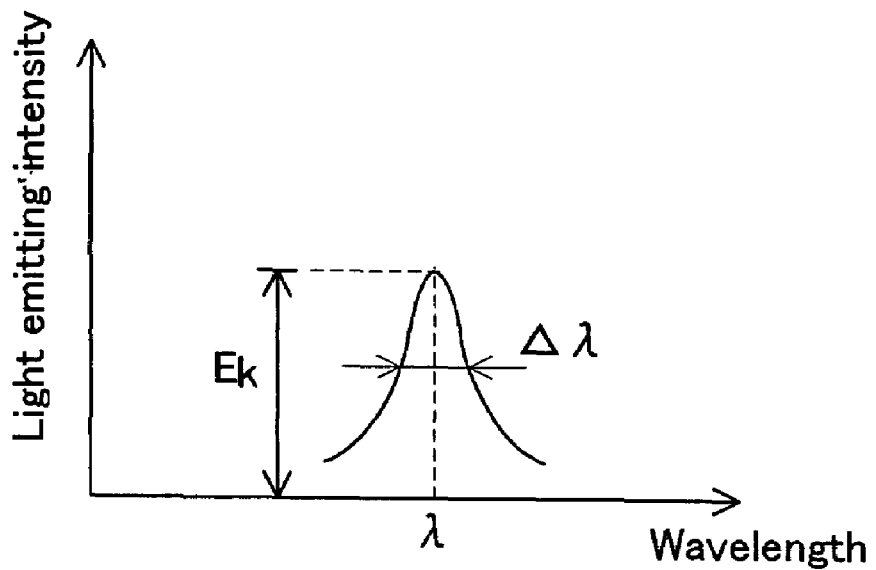
FIG. 1A is a schematic view showing the spectrum exhibited by a conventional information presenting substance.

The information presenting substance-containing material according to the present invention will be explained.

The information presenting substance-containing material contains an information present substance which is a compound including one or more ions selected from the group consisting of a transition element ion having an incomplete 3d shell, a transition element ion having an incomplete 4d shell, a transition element ion having an incomplete 5d shell and a rare-earth element ion and therefore exhibiting one or plural line spectrums and, and wherein the information presenting substance is associated with specific encrypted information corresponding to the one or plural line spectrums.

As the information presenting substance-containing material, other than various plastic materials, paint, ink, fiber, paper and metal can be exemplified. The information presenting substance can be added to the material, or can be introduced in the material in a chemically bonded manner such as a bridged manner or ion bonded manner, or can be applied to the surface of the material.

Especially, in cases where the material is plastic, it is possible to cause the information presenting substance to be easily included in the plastic material at the time of molding the plastic material. In addition, due to the thermoplastic characteristics of the plastic materials, it is impossible to include the information presenting substance in plastic material unless the state of the material is changed by heat after the molding. Therefore, malicious addition of encrypted information by a third party can be prevented.

As the aforementioned compound, an inorganic compound, an organic and inorganic complex compound and an organic compound can be exemplified. Especially, in cases where the compound is an inorganic compound, the information presenting substance is excellent in thermal durability and strong against ultraviolet light.

As the aforementioned information presenting substance, a crystal, an amorphous substance and a complex can be exemplified.

For example, in cases where the information presenting substance is a crystal, the information presenting substance can stably exhibit line spectrums. In the case where the information presenting substance is an amorphous substance, since the line spectrums become complicated, it becomes difficult for a third party to reproduce maliciously, resulting in further enhanced security of the encrypted information included in the material. Furthermore, in the case where the information presenting substance is a complex, since the complex has dye-like characteristics, the information presenting substance becomes readily soluble in organic materials and increases in light emitting intensity of the line spectrums. In addition, in the case where the information presenting substance is a semiconductor, the information presenting substance increases in light emitting intensity of line spectrums.

Since the information presenting substance seldom exists in general material, it becomes possible to decrease the background of the line spectrums. As a result, the detection of the line spectrums can be performed easily even in an environment existing noises generated under various conditions.

The examples of the information presenting substance include, for example, (1) $Y_2O_3$ to which an europium ion ($Eu^{3+}$) is added, (2) $MgAl_{11}O_{19}$ to which a selenium (Se) ion, a terbium (Tb) ion and a manganese ion are added simultaneously, (3) magnesium fluoride ($MgF_2$), zinc fluoride ($ZnF_2$), calcium fluoride ($CaF_2$) or barium fluoride ($BaF_2$) to which nickel ion ($Ni^{2+}$) or cobalt ion ($Co^{2+}$) is added, (4) glass to which a neodymium ion ($Nd^{3+}$), ytterbium ion ($Yb^{3+}$), holmium ion ($Ho^{3+}$) or erbium ion ($Er^{3+}$) is added, (5) magnesium oxide to which a manganese or lithium is added, (6) complex including rare-earth element or the like, and (7) hybrid glass.

Figure 1B:
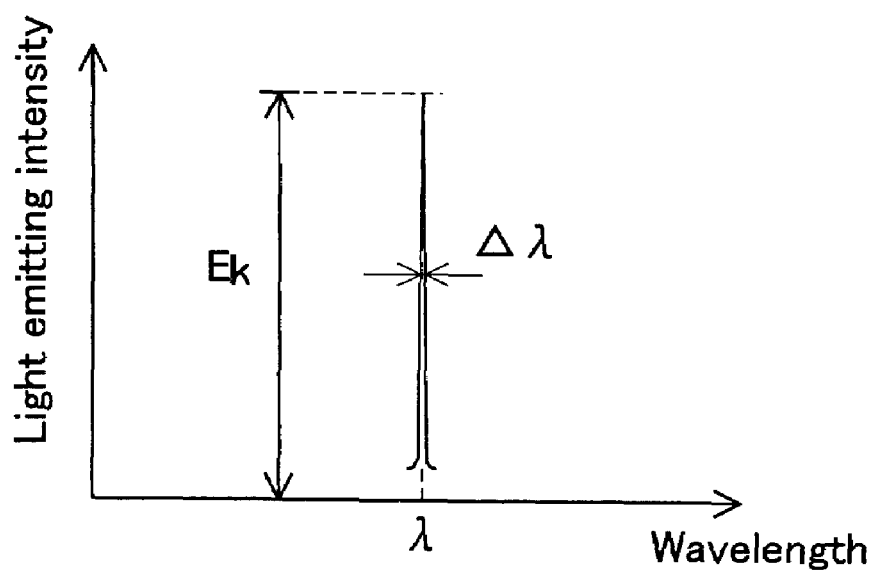
FIG. 1B is a schematic view showing the line spectrum exhibited by an information presenting substance according to an embodiment.

As shown in FIG. 1B, these information presenting substances exhibit a line spectrum narrow in half-width $\Delta\lambda$ and strong in light emitting intensity when irradiated with electromagnetic wave. A line spectrum denotes a spectrum meeting the condition of the following formula [1], preferably formula [2], more preferably formula [3].

$$0 < \Delta\lambda/\lambda < 0.3 \quad [1]$$

$$0 < \Delta\lambda/\lambda < 0.1 \quad [2]$$

$$0 < \Delta\lambda/\lambda < 0.03 \quad [3]$$

wherein $\Delta\lambda$ is a half-width and $\lambda$ is a wavelength of a line spectrum.

Furthermore, the information presenting substance exhibits different line spectrums depending on the type of the compound to which the transition element ion or the rear-earth element ion is included even if the same type and amount of the aforementioned element ion is used.

The mechanism that the information presenting substance emits line spectrums will be explained concretely while exemplifying YAG crystal ($Y_3Al_5O_{12}$) to which an neodymium ion ($Nd^{3+}$) is added.

Figure 2:
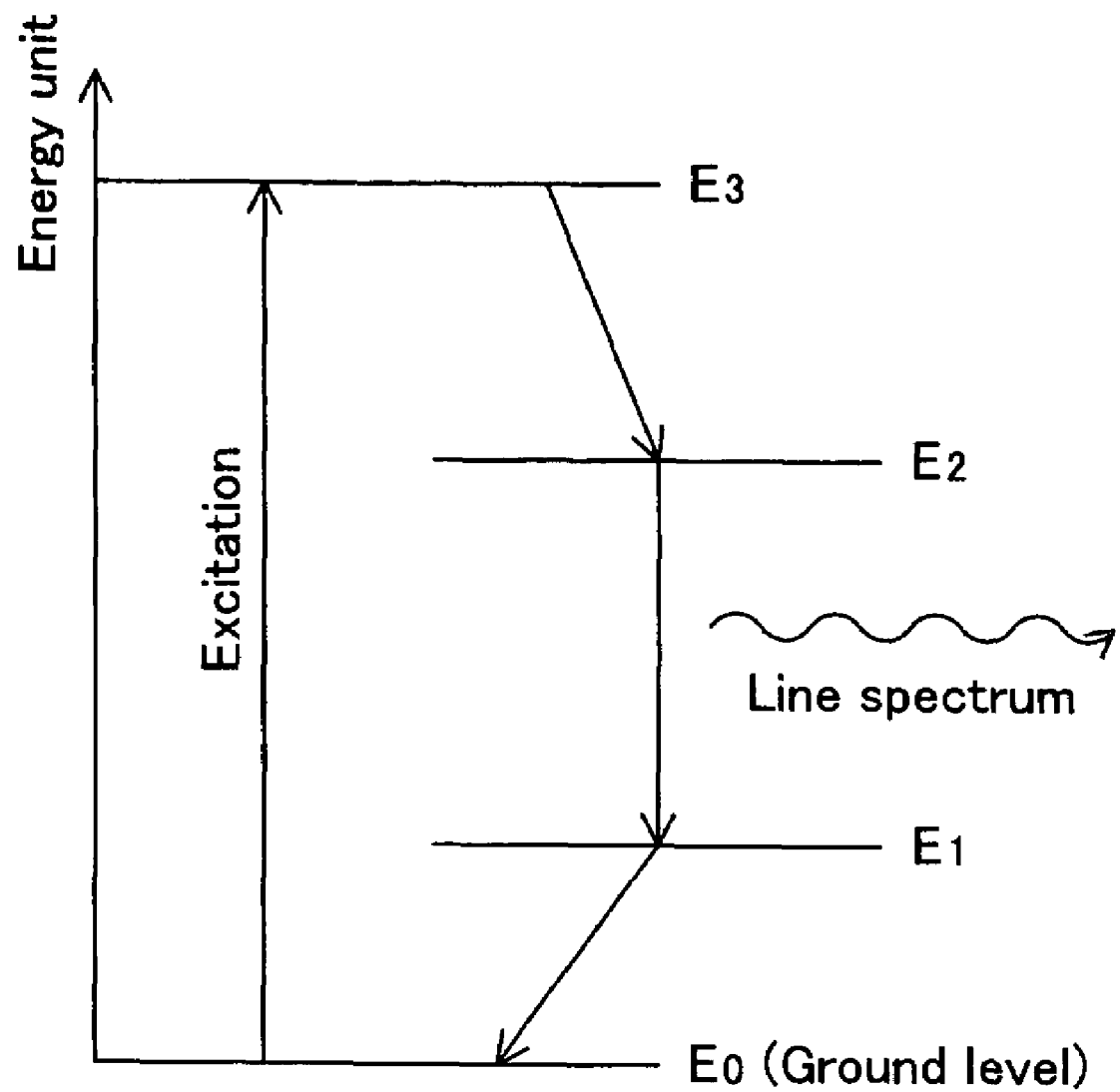
FIG. 2 is an energy level diagram of an neodymium ion in YAG crystal.

FIG. 2 is an energy level diagram of an neodymium ion ($Nd^{3+}$) in YAG crystal ($Y_3Al_5O_{12}$).

In FIG. 2, when near-infrared light is irradiated to the YAG crystal, the neodymium ion in the YAG crystal is excited from the ground level [E0] to the above absorption band [E3], and then quickly drops down to the level [E2] without emitting light (radiationless transition). The time for holding this level [E2] is relatively long, and a line spectrum (near-infrared light) with small half-width and strong light emitting intensity is emitted when transiting to the lower level [E1].

In this embodiment, the explanation is directed to the four energy levels, but not limited thereto. Another information presenting substance having another energy levels can also be applied.

It is preferable that the information presenting substance is included in material within a slight amount range not exerting an influence on the inherent behavior of the material to decrease the influences to the appearance and physicality of the material. Although the slight amount range not exerting an influence on the inherent behavior of the material variously varies depending on the type of materials or the like, the preferable range of the information presenting substance with respect to the material is from 0.01 ppm to 1,000 ppm (including 0.01 ppm and 1,000 ppm), and the more preferable range is from 0.5 ppm to 200 ppm (including 0.5 ppm and 200 ppm).

The aforementioned amount of 0.01 ppm or more is mainly considered sensitivity of a commonly available detecting device. The amount of 1,000 ppm or less is considered so as not to exert an influence on appearance and physicality of most material. The preferable range of 0.5 ppm to 200 ppm is to keep sufficient measuring reliability, reduce the economical burden and minimize the effects on the inherent characteristic of the material.

The method of including the information presenting substance in the material is not specifically limited, and can be any method depending on the type of the material and the information presenting substance. For example, in cases where the material is plastic, a method in which direct molding is performed after performing a dry blend with a drum tumbler, a method in which compound processing is performed with an extruder and a method in which compounding or molding is performed with an internal mixer or a heating roller can be exemplified. A usage after masterbatching can be performed.

The information presenting substance can be used after subjecting to surface finishing using silane coupling agent to enhance the affinity and dispersibility to resin.

To attain an even distribution and dispersion of the information presenting substances in the material at the time of causing the information presenting substances to be included in the material, fatty acid amide, fatty acid metal solt or fatty acid ester can be used as lubricant.

The encrypted information is not specifically limited, and can be information on the material itself such as the type, the production history and the manufacturer of the material and information on the product using the material.

Thus, by including the information presenting substance in material, various encrypted information such as type information, production history information and authentication information can be included in the material.

The line spectrum to be used for specifying the encrypted information is small in half-width and strong in light emitting intensity. Therefore, its identifiability is high, enabling the encrypted information included in the material to be simply and assuredly identified, which results in an easy and assured identification of the material.

Furthermore, even if the same type and amount of the aforementioned element ion is used, the information presenting substance exhibits different line spectrum depending on the type of the compound in which the element ion is included. Accordingly, by combining the element ion and the compound, a large variety of line spectrums can be created, enabling various encrypted information to be included in the material.

Furthermore, since the transition element ion or the rear-earth element ion to be added seldom exists in general material, a desired line spectrum can be detected even in an environment existing noises generated under various conditions.

Identifying the information presenting substance-containing material is performed by: storing the line spectrum and the encrypted information in a storing means in an associated manner; irradiating electromagnetic wave in a predetermined wavelength area to the information presenting substance; detecting the line spectrum emitted from the information presenting substance in accordance with the irradiation of the electromagnetic wave, and then identifying the corresponding encrypted information based on the detected line spectrum.

For example, as shown in the following Table 1, in the case where the line spectrums (wavelength X, wavelength Y, wavelength Z) and the encrypted information (material a, material b, material c) are associated with each other, when the line spectrum of wavelength X, wavelength Y or wavelength Z is detected from the material, the corresponding encrypted information of the material a, b or c can be specified.

TABLE 1

| | Wavelength of line spectrum | | |
|---|---|---|---|
| | X | Y | Z |
| Type of material | a | b | c |

Furthermore, as shown in the following Table 2, in the case where the line spectrums (light emitting intensity α, light emitting intensity β, light emitting intensity γ) and the encrypted information (manufacturer A, manufacturer B, manufacturer C) are associated with each other, when the line spectrum of light emitting intensity α, light emitting intensity: β or light emitting intensity γ is detected from the material, the encrypted information of the corresponding manufacturer A, B or C can be specified.

TABLE 2

| | Light emitting intensity of line spectrum | | |
|---|---|---|---|
| | α | β | γ |
| Manufacture of material | A | B | C |

Regarding the corresponding relationship between the line spectrums and the encrypted information, in the above explanation, the spectrum itself and the encrypted information are associated with each other. However, the content or type of the information presenting substance to be derived from the line spectrum and the encrypted information can be associated with each other.

Furthermore, the encrypted information can be associated with a plurality of line spectrums and represented by plural digit numeric data in which each digit of the numeric data corresponds to the wavelength of each line spectrum and a value of each digit corresponds to the light emitting intensity of each line spectrum.

For example, as shown in the following Table 3, in the case where each digit of the encrypted information corresponds to each wavelength X, Y or Z of the line spectrums and the value of each digit corresponds to each light emitting intensity of the line spectrums, the numeric data of the encrypted information can be specified by measuring the light emitting intensity of each wavelength X, Y and Z of the line spectrums.

With this, the line spectrum group consisting of a plurality of line spectrums can be used like a bar-code, enabling plural digit numeric encrypted information to be included in the material. Especially, when the numeric data is used as an ID number, an ID card highly effective for preventing forgery can be provided.

In the example shown in Table 3, the numeral obtained by multiplying the content (peak value) of the information presenting substance by 10 and rounded is used as the numeric data.

TABLE 3

|  | Wavelength of line spectrum | | |
| --- | --- | --- | --- |
|  | X | Y | Z |
| Light emitting intensity of line spectrum | 0.294 | 0.336 | 0.109 |
| Encrypted information (numeric data) | 3 | 3 | 1 |

[Identification System]

Next, an identification system for identifying the information presenting substance-containing material will be explained with reference to FIGS. 3 to 6.

Figure 3:
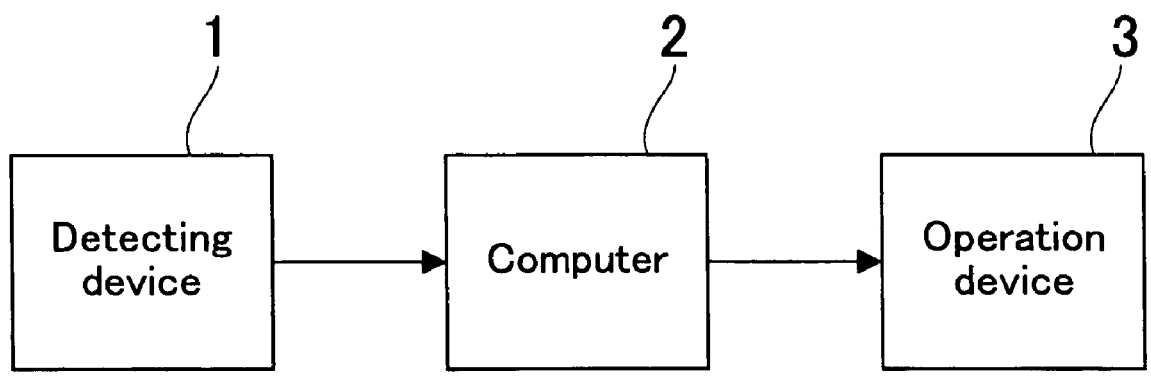
FIG. 3 is a schematic structural view of an identification system.

As shown in FIG. 3, this identification system is provided with a detecting device 1 for detecting the line spectrum of the information presenting substance included in the material, a computer 2 for identifying the material based on the detected line spectrum detected by the detecting device 1, and an operation device 3 such as a fluorescence spectrum displaying device for performing a predetermined operation based on the identified result by the computer.

The detecting device 1 irradiates an electromagnetic wave within a predetermined wavelength region, preferably electromagnetic wave within a wavelength region covering from ultraviolet light to infrared light, more preferably electromagnetic wave within a wavelength region covering from ultraviolet light to near-infrared light, to the information presenting substance-containing material, and detects the line spectrum exhibited from the information presenting substance in accordance with the irradiation. A detecting device 1 employing techniques such as spectroscopy system by a CCD, time-resolved spectral diffraction or modulation spectral diffraction is preferably used.

Figure 4:
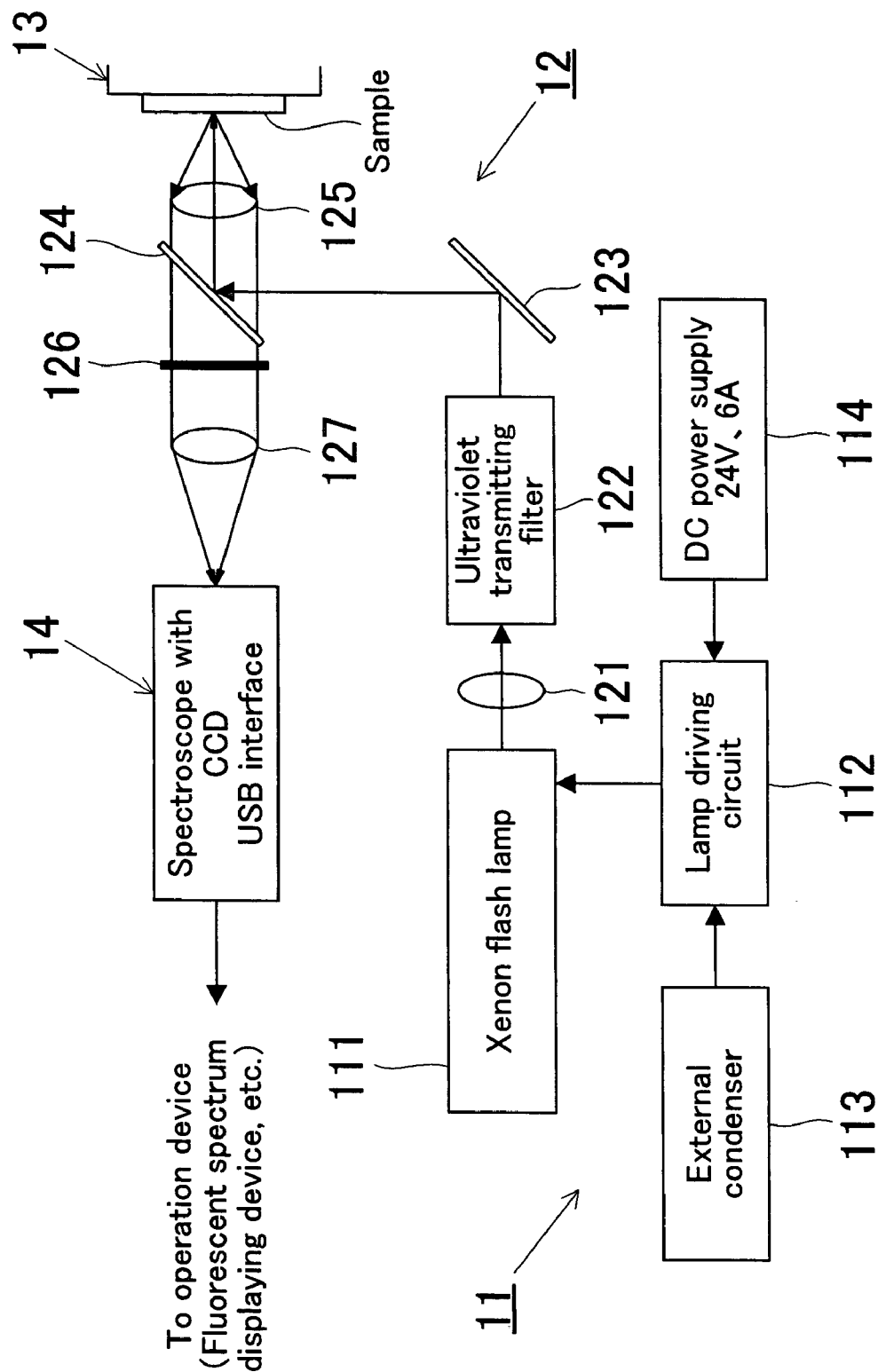
FIG. 4 is a schematic view showing the hardware structure of the identification device shown in FIG. 3.

FIG. 4 illustrates an example of a hardware of the detecting device 1.

The detecting device 1 is provided with an excitation light source 11, various optical systems 12, a sample stage 13 and a spectroscope 14.

The excitation light source 11 is provided with a xenon flash lamp 111, a lamp driving circuit 112, an external condenser 113 and a DC power supply 114. The xenon flash lamp 111 has a reflecting mirror inside thereof, and the specification is as follows: the maximum mean input energy is 1 J; the maximum mean input is 60 w; the maximum repeating frequency is 60 Hz (if the maximum mean input is 60 w or less, it is operable up to 100 Hz); and the half-width of the pulse width of the light emission is 2.9 micro second (where 2 µF, 1,000V).

The exciting pulse light from the xenon flash lamp 111 is formed into parallel light by the lens 121, and then the light having a wavelength component in a ultraviolet region required to excite the sample is selected by a reflection type ultraviolet transmitting filter 122 and transmitted therethrough. The transmitted light is reflected by the reflection mirror 123 and the half mirror 124 and then condensed by the lens 125 to be irradiated to the sample. The half mirror 124 has a combination of a function of irradiating only the ultraviolet light to the sample by reflecting the exciting light and a function of transmitting only the emission component within the visible range to the spectroscope 14. The lens 125 has a combination of a function of condensing the ultraviolet light into the sample and a function of forming the emission component from the sample into parallel light.

The light emission from the sample is transmitted through the half mirror 124 and the visible light transmitting optical filter 126 (transmitting the light with a wavelength of 400 nm or above) and then condensed by the lens 127 into the slit of the spectroscope 14.

The spectroscope 14 is a polychromator employing an advanced monkgirison mount covering the visible range waveband nevertheless the small size, and includes an entrance slit, a concave mirror, a diffraction grating and a line sensor made of a CCD element. The fluorescent light condensed by the lens 127 on the slit of the spectroscope 14 is divided into respective wavelengths by the grating in the spectroscope 14 and then converted into analog signals by the line sensor. Thereafter, the analog signals are converted into digital signals by an A/D converter circuit to be transmitted to the computer 2 as line spectrum data.

Figure 5:
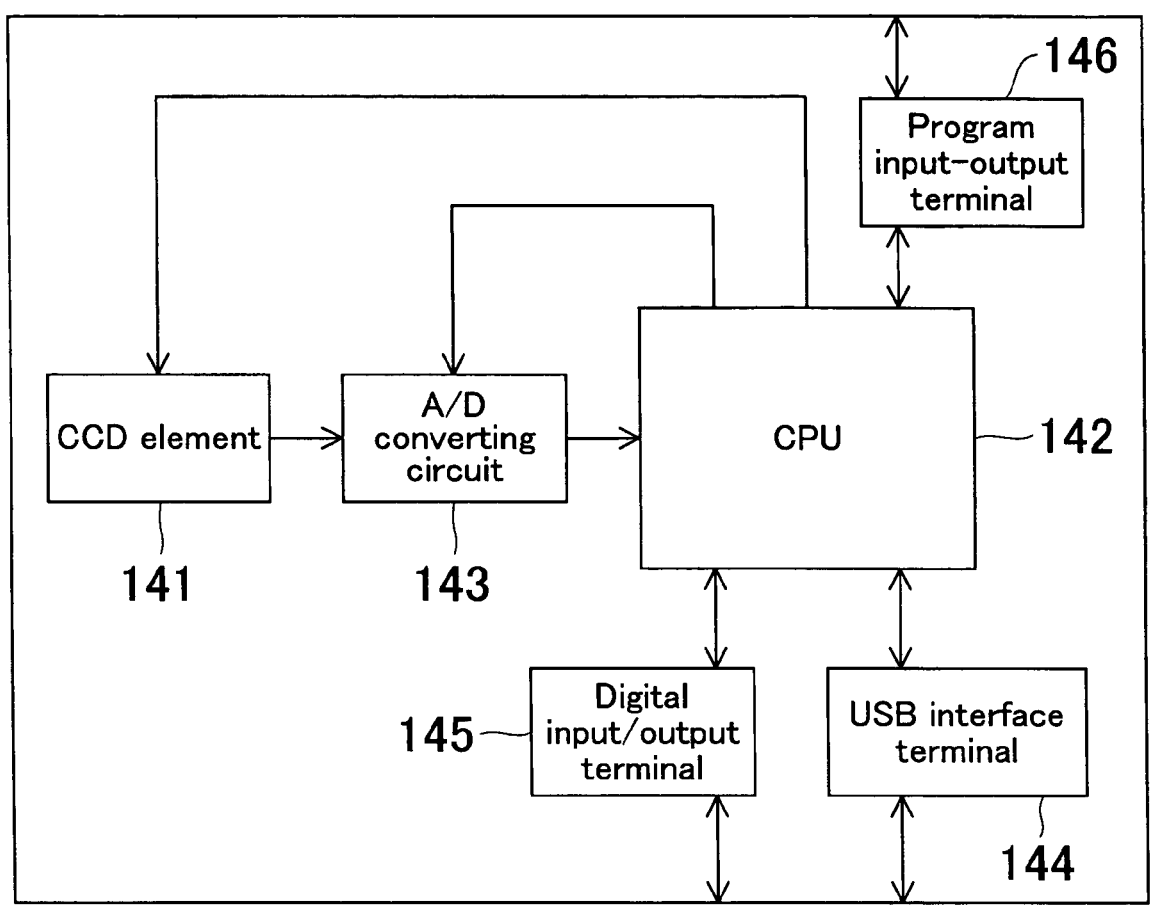
FIG. 5 is a schematic view showing the electric structure of the detecting device shown in FIG. 3.

FIG. 5 shows an electric structure of the spectroscope 14.

The spectroscope 14 has a function of storing charge corresponding to the amount of light entered into the CCD element 141 when fluorescent light from the sample is entered into the CCD element 141 and transferring the charge to an electric circuit connected to the outside. In accordance with the control pulse from the CPU 142, the output from the CCD element 141 is converted into a digital signal by the A/D converting circuit 143 and then inputted into the CPU 142 as serial data. The data inputted into the CPU 142 is subjected to a serial-USB conversion, and then transmitted to the computer via the USB interface terminal 144. The CPU 142 is provided with a general-purpose digital input-output terminal 145 for controlling the xenon flash lamp 111 or inputting/outputting a synchronizing pulse or trigger for a device connected to an outside. The CPU 142 is operated by a program written therein. The CPU is provided with a program input-output terminal 146 for rewriting the program. Therefore, the function of the CPU 142 can be changed by changing the program.

Figure 6:
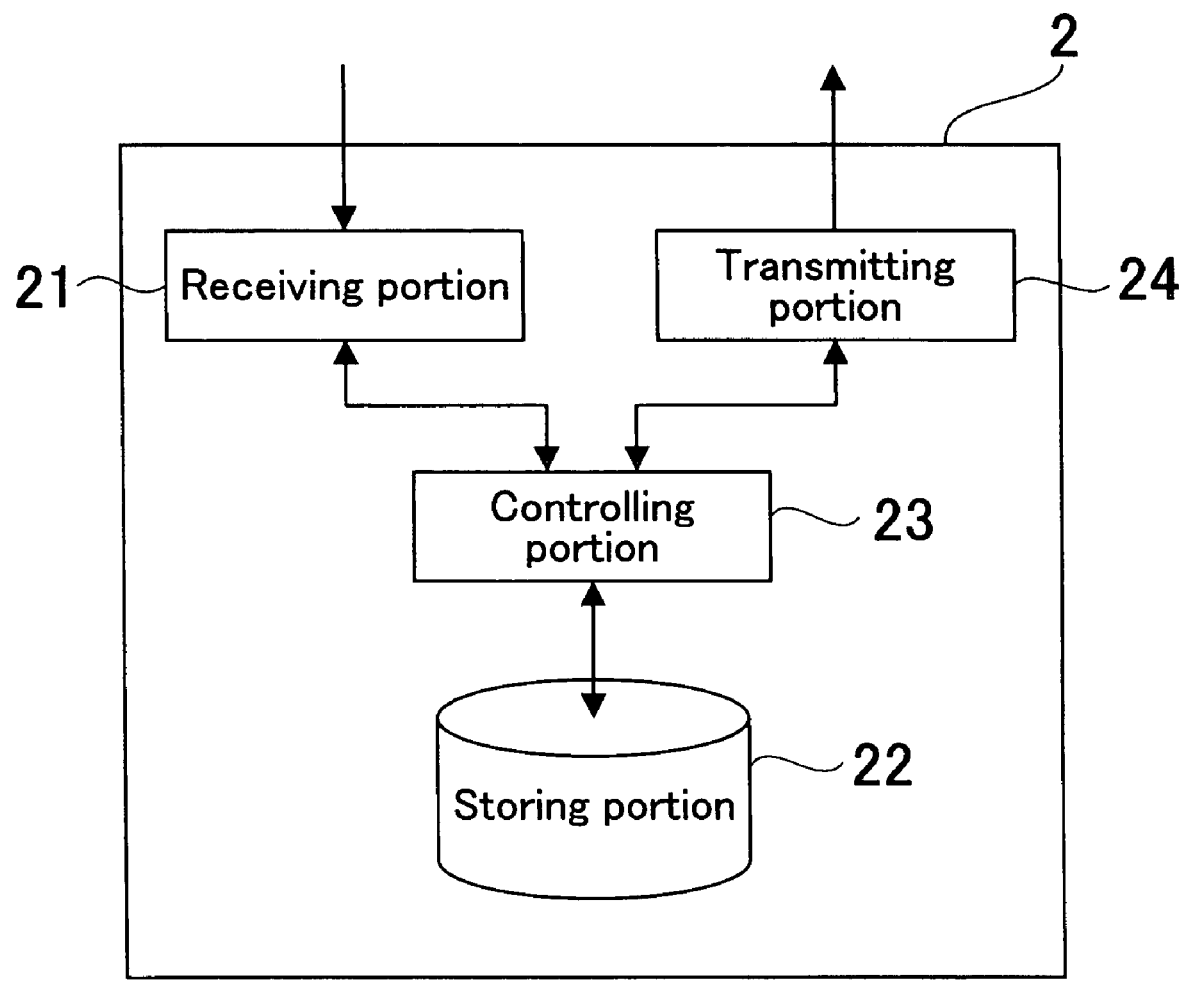
FIG. 6 is a schematic view showing the electric structure of the computer shown in FIG. 3.

As shown in FIG. 6, the computer 2 is provided with a receiving portion 21 for receiving the line spectrum data transmitted from the detecting device 1, a storing portion 22 for storing the line spectrum and the encrypted information in an associated manner, a controlling portion 23 having a function of identifying the material by specifying the corresponding encrypted information from the storing portion 22 based on the line spectrum data, and a transmitting portion 24 for transmitting predetermined information to the operation device 3 depending on the identified result of the material.

In identifying the material by the controlling portion 23, the measured one optical spectrum or displayed graph can be decomposed into several types of components by a least square method or the like using a conventionally available spectroscopic analysis software or graph displaying software to display the result. By using line spectrum data previously detected and stored, it can be equipped with a function of analyzing using a least square method so as to reproduce the newly detected line spectrum.

[Operation of Identification System]

Figure 7:
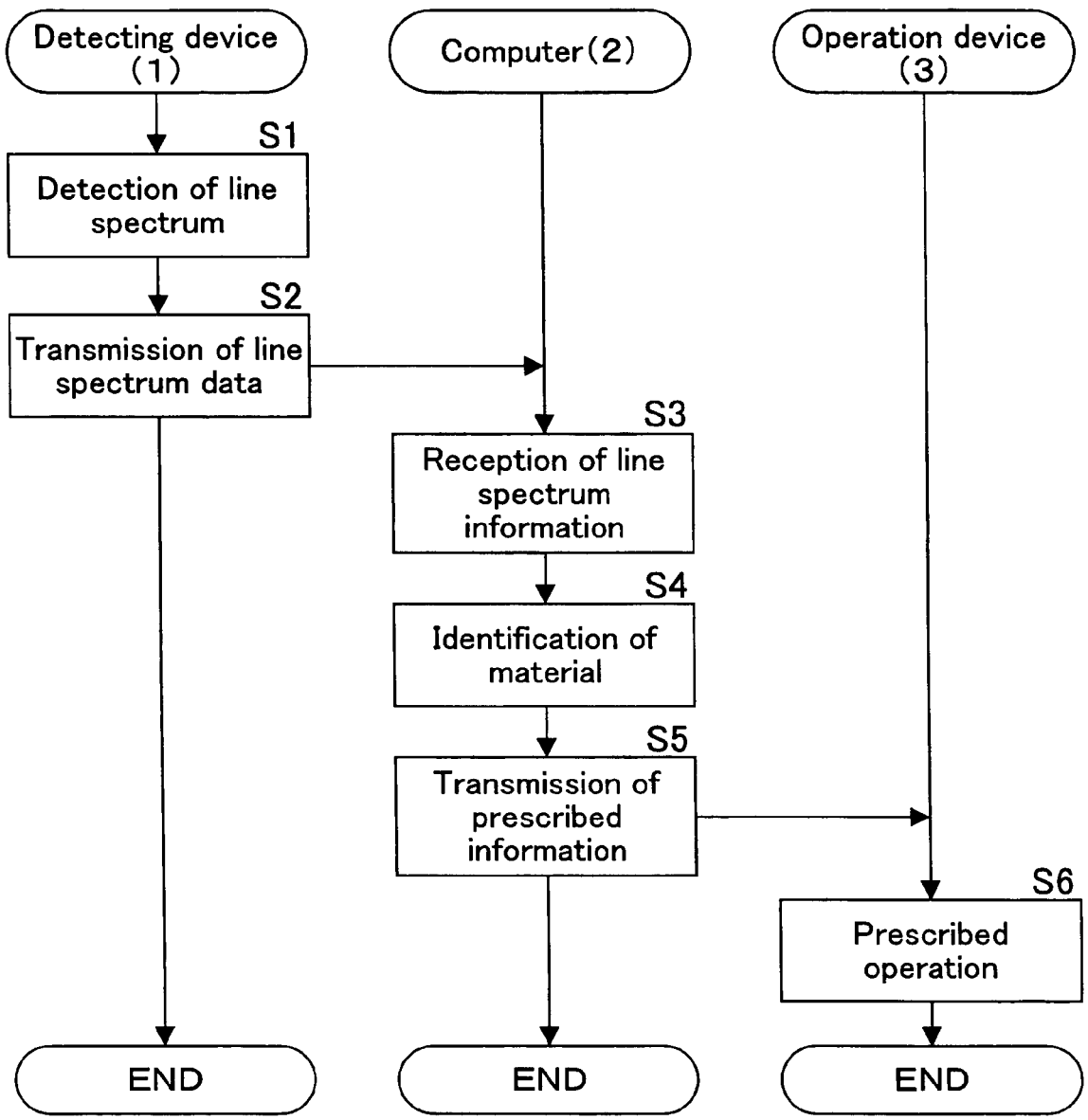
FIG. 7 is a flowchart showing the operation of the identification system shown in FIG. 3.
Figure 8:
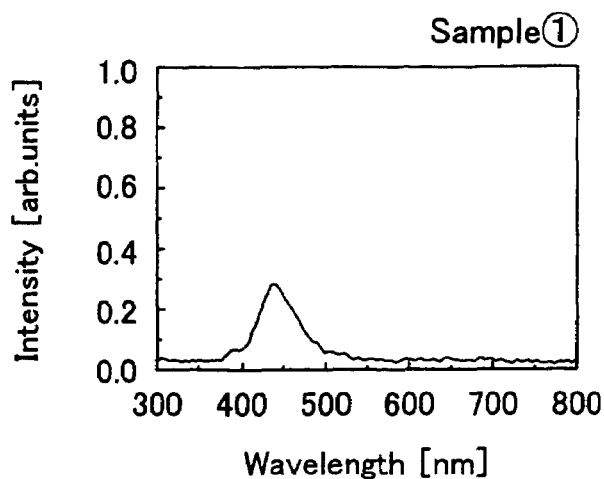
FIG. 8 shows the line spectrum of the test piece (1).
Figure 9:
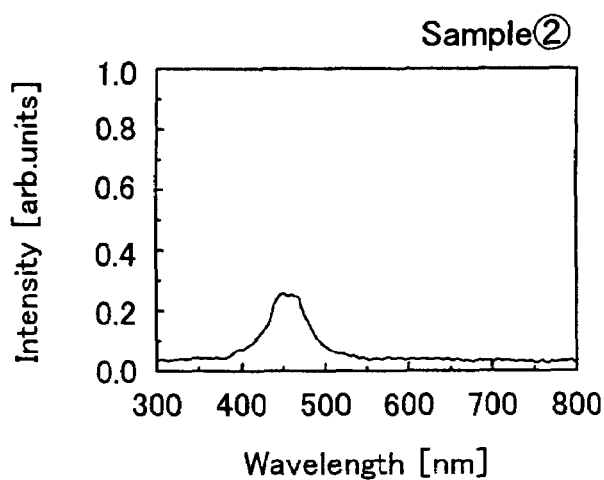
FIG. 9 shows the line spectrum of the test piece (2).
Figure 10:
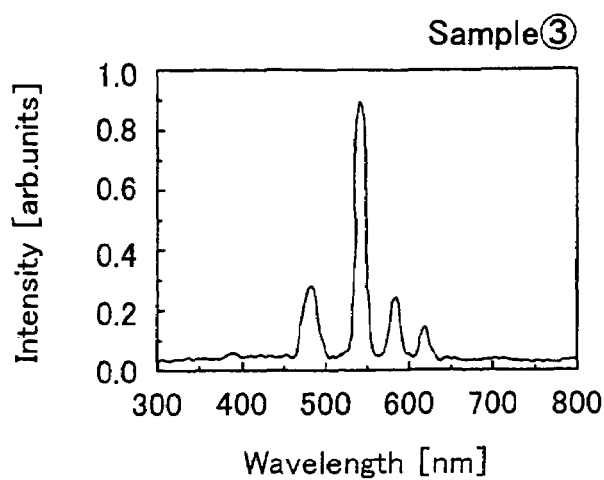
FIG. 10 shows the line spectrum of the test piece (3).
Figure 11:
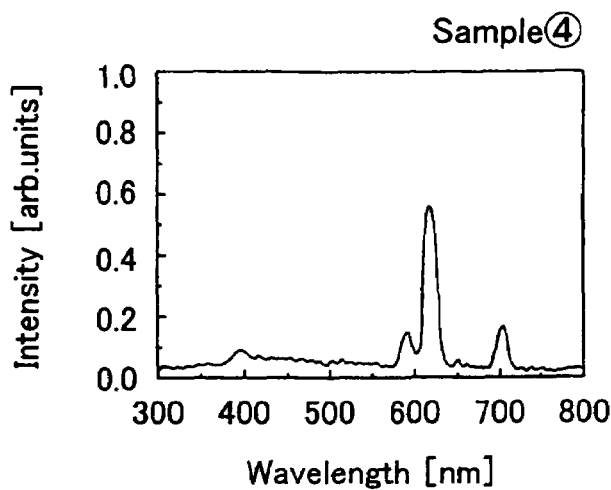
FIG. 11 shows the line spectrum of the test piece (4).

Next, an operation of the aforementioned identification system will be explained with reference to the flowchart shown in FIG. 7. In the following explanation and drawings, "Step" will be abbreviated as "S."

In the detecting device 1, an electromagnetic wave within a predetermined wavelength region, preferably electromagnetic wave within a wavelength region covering from ultraviolet light to infrared light, more preferably electromagnetic wave within a wavelength region covering from ultraviolet light to near-infrared light, is irradiated to the information presenting substance-containing material disposed on the sample stage 13, and the line spectrum exhibited from the information presenting substance in accordance with the irradiation is detected (S1).

The detecting device 1 performs A/D conversion of the detected line spectrum and then transmits the converted data to the computer 2 as line spectrum data (S2).

Next, in the computer 2, the receiving portion 21 receives the line spectrum data transmitted from the line detecting device 1 (S3).

Then, the controlling portion 23 identifies the material by specifying the corresponding encrypted information based on the line spectrum data (S4).

The transmitting portion 24 transmits a prescribed information depending on the identification result of the material by the controlling portion 23 (S5).

Thereafter, the operation device 3 receives the prescribed information transmitted from the computer 2 and performs prescribed operations such as a display of various screens or an identification based on the received prescribed information.

At the time of detecting the line spectrum emitted from the information presenting substance, noises around the targeted line spectrum can be cut with a filter, or modulation can be performed.

Some light emission of the information presenting substance may have a longer life than the background light emission, and therefore the detection of line spectrum can be performed at a certain time later.

Although the detecting device 1, the computer 2 and the operation device 3 are constituted separately, at least two of them can be integrated into a single device.

In cases where an optical fiber is used, the detecting device can detect the line spectrum of the information presenting substance located at the inside of the object to be identified via a small gap.

EXAMPLE

Example 1

Next, concrete examples according to the present invention will be explained.

As information presenting substance-containing materials, samples (samples 1 to 9) shown in Table 4 were prepared. These samples were materials in which one or a plurality of fluorescent substances (fluorescent substance A, fluorescent substance B, fluorescent substance C, fluorescent substance D, fluorescent substance E), fluid paraffin and magnesium stearate (ST-Mg) shown in Table 4 were added to polypropylene resin. The samples 1 to 9 were formed into a rectangle shape of 10 cm length×5 cm width×about 2 mm thickness, respectively.

The amount of each fluorescent substance was shown by weight percentage with respect to 100-gram polypropylene resin. As shown in Table 5, each fluorescent substance was a substance in which a rear-earth ion was added to a host crystal. Since the amount of added fluorescent substance is a total of the host crystal and the rear-earth ion, it is considered that the amount of the actually added rear-earth ion is smaller than that shown in Table 4.

TABLE 4

| | 1 | 2 | 3 | 4 | 5 | 6 | 7 | 8 | 9 |
|---|---|---|---|---|---|---|---|---|---|
| Fluorescent substance A | 0.01 | | | | | | | | |
| Fluorescent substance B | | 0.01 | | | 0.01 | | | 0.001 | |
| Fluorescent substance C | | | 0.01 | | 0.01 | 0.01 | 0.01 | | 0.001 |
| Fluorescent substance D | | | | 0.01 | | 0.01 | 0.01 | 0.001 | 0.001 | 0.01 |
| Fluorescent substance E | | | | | | 0.01 | | | |
| Fluid paraffin | 0.1 | 0.1 | 0.1 | 0.1 | 0.1 | 0.1 | 0.1 | 0.1 | 0.1 |
| St-Mg | 0.1 | 0.1 | 0.1 | 0.1 | 0.1 | 0.1 | 0.1 | 0.1 | 0.1 |

[unit: %]

TABLE 5

| Fluorescent Substance | Host crystal | Rear earth ion | Wavelength of main line spectrum |
|---|---|---|---|
| Fluorescent substance A | $(Sr,Ca,Ba)_5(PO_4)Cl$ | Eu | 440 nm |
| Fluorescent substance B | $BaMg_2Al_{16}O_{27}$ | Eu | 450 nm |
| Fluorescent substance C | $LaPO_4$:Ce | Tb | 543 nm |
| Fluorescent substance D | $Y(P,V)O_4$ | Eu | 619 nm |
| Fluorescent substance E | $Y_2O_3$ | Eu | 611 nm |

The fluorescent spectrums corresponding to each of Samples 1 to 9 are shown in FIGS. 8 to 16. The fluorescent intensity of each fluorescent spectrum is standardized such that the peak intensity of Sample 7 (shown in FIG. 14) is considered to be 1.

Samples 1 to 4 were substances in which one of fluorescent substances A, B, C and D was added to polypropylene resin. Samples 5 and 6 were substances in which three types of fluorescent substances were added at the same density to polypropylene resin. Samples 7 and 9 were substances in which two types of fluorescent substances different in density were added to polypropylene resin. Sample 8 was a substance in which two types of fluorescent substances different in density were added to polypropylene resin.

Figure 12:
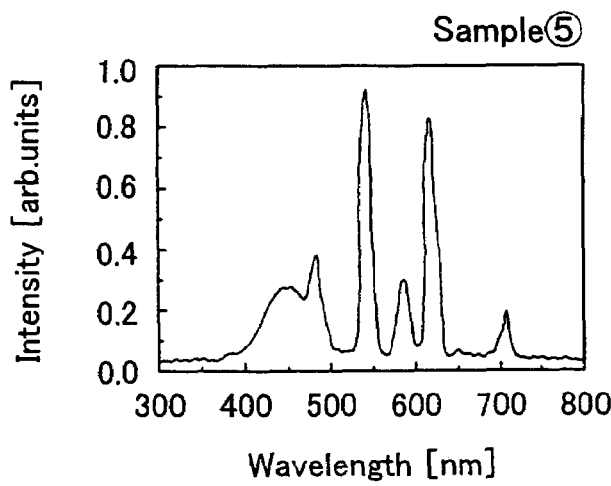
FIG. 12 shows the line spectrum of the test piece (5).
Figure 13:
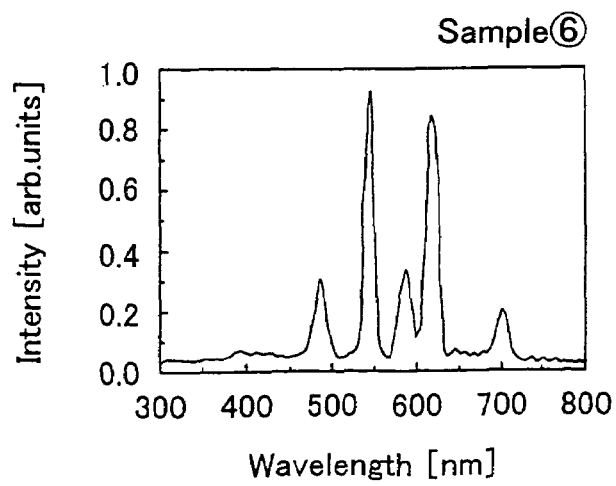
FIG. 13 shows the line spectrum of the test piece (6).
Figure 14:
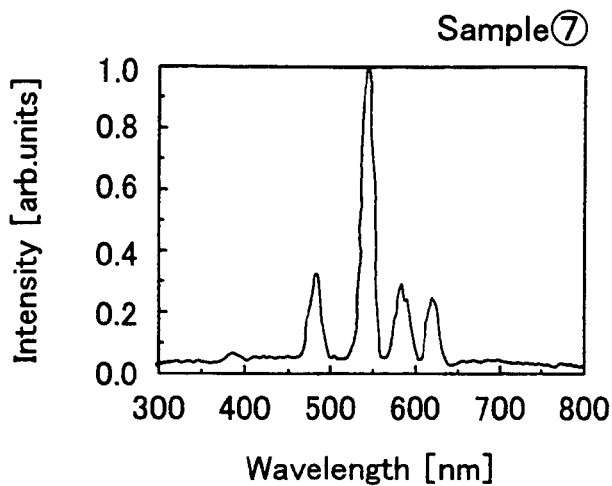
FIG. 14 shows the line spectrum of the test piece (7).
Figure 15:
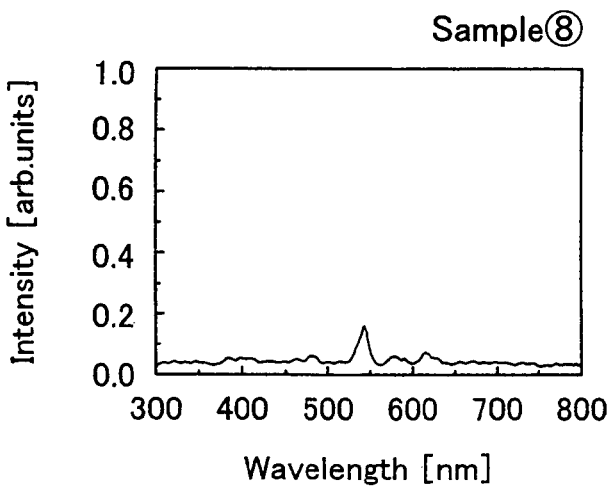
FIG. 15 show the line spectrum of the test piece (8).
Figure 16:
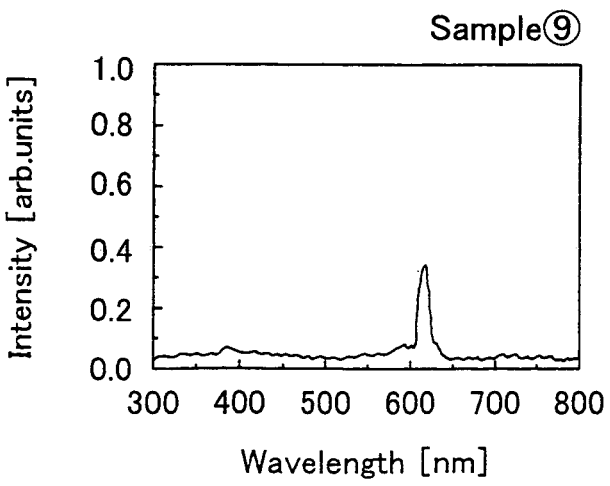
FIG. 16 shows the line spectrum of the test piece (9).

For example, in Sample 5, three types of fluorescent substances B, C and D of the same density of 0.01% (100 ppm), fluid paraffin and magnesium stearate (St-Mg) were added in polypropylene resin. As shown in FIG. 12, the measured line spectrum of Sample 5 exhibits a fluorescent spectrum obtained by overlapping three types of separately measured fluorescent spectrums corresponding to the fluorescent substances B, C and D and shown in FIG. 9, FIG. 10 and FIG. 11 respectively.

As shown in FIGS. 8 to 16, from the observed results of the fluorescent spectrums of Samples 1 to 9, it is confirmed that line spectrums each having a narrow wavelength $\Delta \lambda$ is generated. Especially, as shown in FIGS. 10 to 14, from the observed results of the fluorescent spectrums of Samples 3 to 7, it is confirmed that line spectrums each having a very narrow wavelength $\Delta \lambda$ is generated.

Fluorescent spectrums of three types of samples in which 1 ppm, 10 ppm and 100 ppm of fluorescent substance D were added to polypropylene resin respectively were measured. Then, the concentration effect of the fluorescent intensity was observed.

Figure 17:
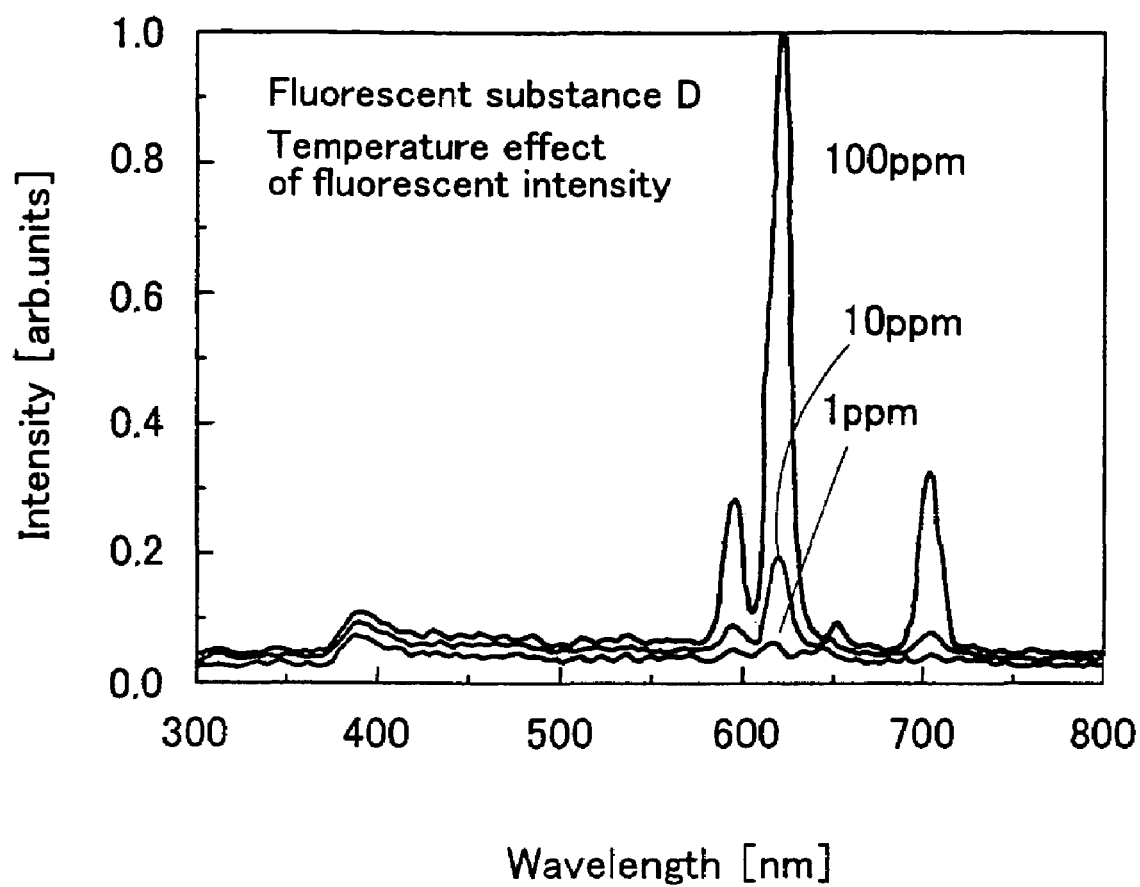
FIG. 17 shows the line spectrums of three types of test pieces, or three test pieces in which fluorescent substance D of 1 ppm, 10 ppm and 100 ppm are added to polypropylene resin respectively.
Figure 18:
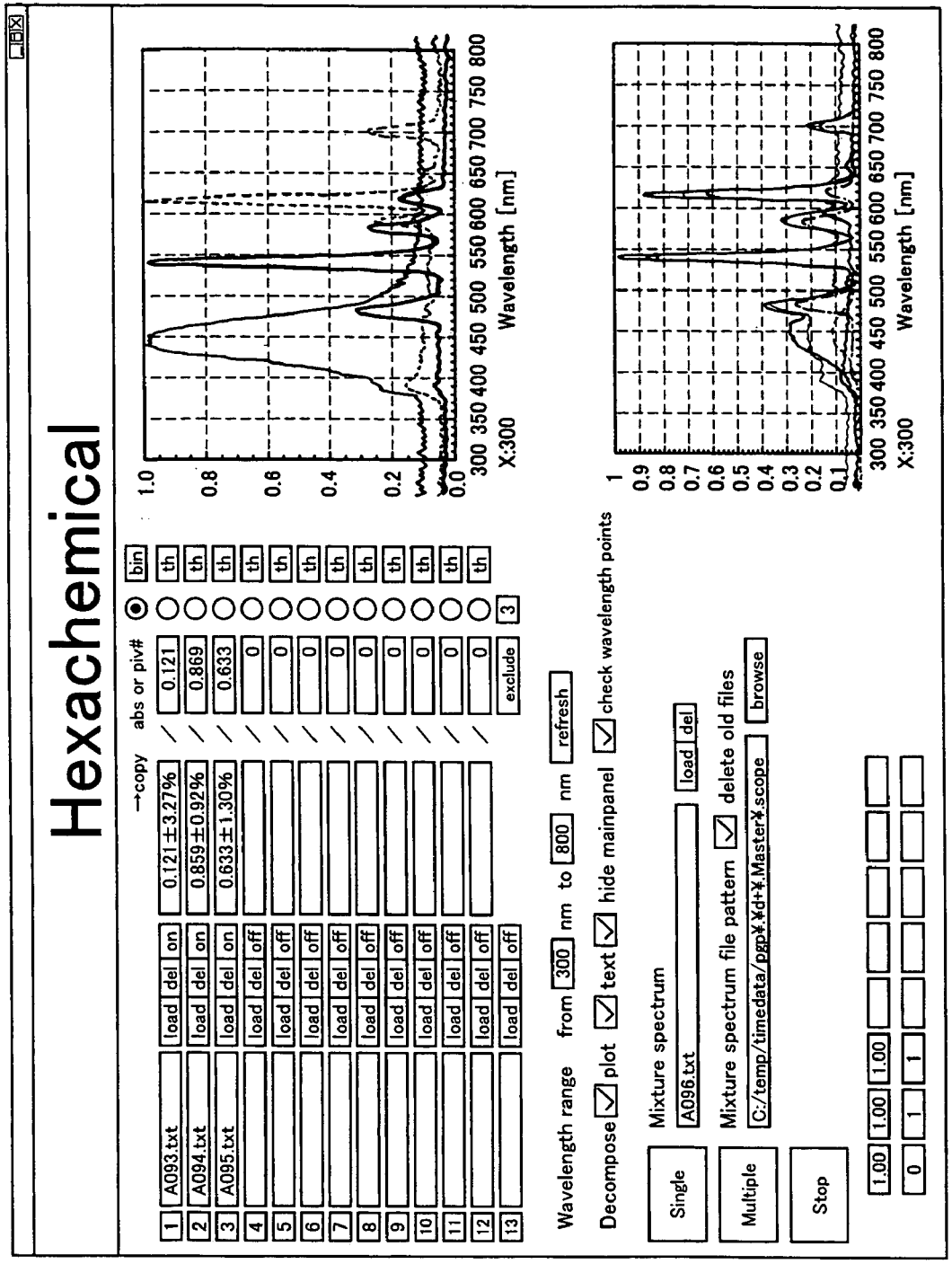
FIG. 18 shows an example of the analysis and the display of spectrum data.

As a result, as shown in FIG. 17, even in the state in which the excitation power of the xenon flash lamp is decreased, it was possible for the sample in which the fluorescent peak (line spectrum) by Eu having a wavelength of 619 nm was 1 ppm to be sufficiently observed.

An example of procedure for identifying the manufacturer's name, the type, the production place of an industrial product by adding several types of fluorescent substances to the product by observing the fluorescent spectrum will be as follows.

(1) Determining an industrial product to which fluorescent substances are to be added.

(2) Determining the type and concentration of the fluorescent substances to be added. For example, the fluorescent substance 1 (concentration: 100 ppm), fluorescent substance 2 (concentration: 10 ppm).

(3) Adding the determined fluorescent substance 1 and fluorescent substance 2 to the industrial product.

(4) Adding the fluorescent substance 1 (concentration: 100 ppm) and the fluorescent substance 2 (concentration: 10 ppm) respectively to products having the same material and type as the industrial products to which fluorescent substances are added.

(5) Measuring the line spectrum of the product to which only the fluorescent substance 1 was added. The measured line spectrum will be referred to as "line spectrum 1."

(6) Similarly, measuring the line spectrum of the product to which only the fluorescent substance 2 was added. The measured line spectrum will be referred to as "line spectrum 2."

(7) Measuring the line spectrum of the industrial product to which the fluorescent substance 1 and the fluorescent substance 2 were simultaneously added. The measured line spectrum will be referred to as "line spectrum 3."

(8) When measuring the line spectrum, it is required to perform the measurements under the same conditions. Since the fluorescence intensity strongly depends on the excitation wavelength especially, when measuring the line spectrums 1, 2 and 3, a light source having the same excitation wavelength and the same excitation wavelength width should be used.

(9) In advance, storing the measured line spectrums 1 and 2 in a database as data.

(10) When reading the stored line spectrums 1 and 2 using prescribed program, the respective line spectrums of the fluorescent substances 1 and 2 are displayed on the right upper side of the screen.

(11) Reading out the measured line spectrum 3 on the "Single" column on the screen.

(12) Clicking the "Single" column on the screen.

(13) A line spectrum calculated so as to reproduce the spectrum shape of the line spectrum 3 using the line spectrum shape of the previously read line spectrums 1 and 2 will appear on the right lower side of the screen.

(14) In addition, the component ratio of the line spectrums 1 and 2 for reproducing a line spectrum and the error caused at the time of reproducing will be displayed at the right side of the data display column read the line spectrums 1 and 2. Furthermore, the line spectrum which is a result representing the line spectrum using the component ratio of the determined line spectrums 1 and 2 will be displayed over the line spectrum 3.

(15) Furthermore, the threshold for judging the ratio of the line spectrums 1 and 2 to reproduce the line spectrum 3 can be arbitrarily set. The setting of the threshold is a function of eliminating the corresponding line spectrum if the error is large.

By following the aforementioned procedures, from the known line spectrums 1 and 2, it is possible to judge in the line spectrum 3 observed from the product how accurately fluorescent substances 1 and 2 are added. The aforementioned product confirming process is one example, and therefore the sequence, of the method, the means and the procedure can be changed.

It is effective to select a specific excitation wavelength and then selectively excite it.

In the above example, an example in which the overlapping of spectrums is small is shown. However, since both the case in which the spectrum pattern in which different types of line spectrums are overlapped intricately and the case in which a single line spectrum and the spectrum pattern are overlapped are saved in the storing means as reference signals, by comparing the signal patterns of the detected encrypted information, the pattern can be separated into single spectrum or plural spectrums, which in turn enables the reading of the encrypted information.

The device used in the example is described as follow.

Koken Kogyo Kabushiki Kaisha
Spectroscope: MG-30

TABLE 6

| Optical type | Improved monk · girison · mount |
|---|---|
| Grating ruling number | 600 line/mm |
| Reciprocal dispersion | 25.8 nm/mm |
| Half-width | 10 nm (at the time of 0.1 mm slit) |
| Wavelength accuracy | ±1 nm |
| Collimator | Focal distance f = 30 mm |

TABLE 6-continued

| Optical type | Improved monk · girison · mount |
|---|---|
| Outside dimension | 65 W × 45 H × 75 D mm |
| Weight | About 700 g |

Hamamatsu Phoyonisc Kabushiki Kaisha
Xenon flash lamp L7685
Power source for lamp C6096
External condenser E7289-01 (2 μF)
Trigger socket E6647
Cooling jacket E6611

Sigma Kohi Kabushiki Kaisha
    Lens 1 Plano-convex quartz lens
        (Focal distance f=30 mm, Diameter φ15 mm)
    Lens 2 Piano-convex quartz lens
        (Focal distance f=30 mm, Diameter φ15 mm)
    Lens 3 Visible achromatic lens
        (Focal distance f=30 mm, Diameter φ15 mm)
Reflecting mirror Flat mirror Diameter φ30 mm Asahi Spectra Kabushiki Kaisha
Ultraviolet transmitting filter UV-B (reflection type)
Half mirror DML-0350 (Diameter φ32 mm)
Filter LU0400 25 mm angle (square)

Sony
ILX554B (CCD for bar-code reader)
    Effective pixel number 2048 pixels
    Pixel size 14 μm×56 μm
    5V Single power supply
CCD control circuit
    MAXIM JAPAN KABUSHIKI KAISHA A/D converting circuit MAX1284
    Digital input/output circuit MAX488
    IBI KABUSHIKI KAISHA CPU/USB circuit USB232/AT90S2313

Embodiment 2

Hereinafter, another concrete embodiment will be explained.

In this embodiment, fluorescent spectrums of three types of samples in which the aforementioned fluorescent substance D of 1 ppm, 10 ppm, 100 ppm is added respectively to polycarbonate were measured.

Figure 19:
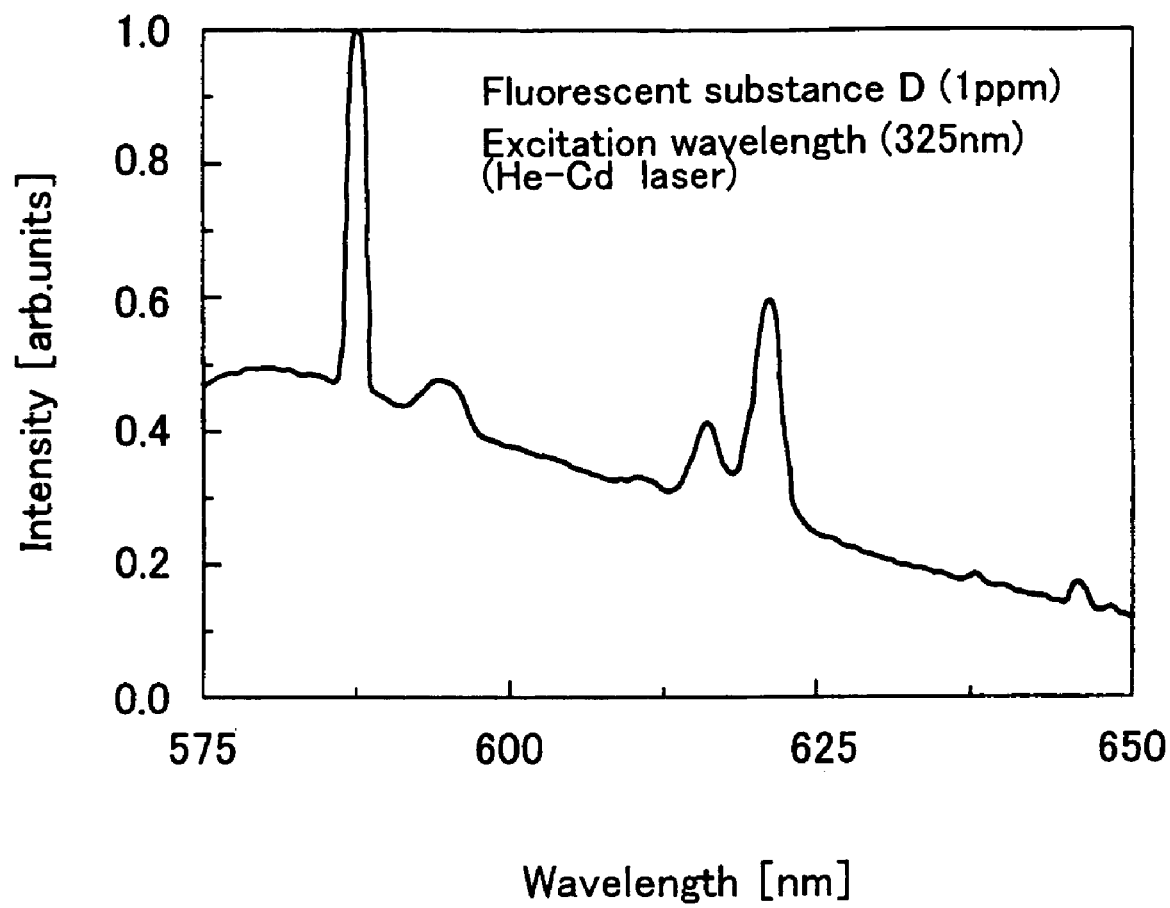
FIG. 19 shows the fluorescent spectrum of the test piece in which the fluorescent substance D of 1 ppm is added to polycarbonate resin.

As a result, the fluorescent intensity decreased as compared to polypropylene resin. However, by increasing the intensity of the excitation light source and the accuracy of the photodetector, as shown in FIG. 19, the fluorescent peak (line spectrum) of Eu having the wavelength of 619 nm was sufficiently observed from the sample of 1 ppm.

Figure 20:
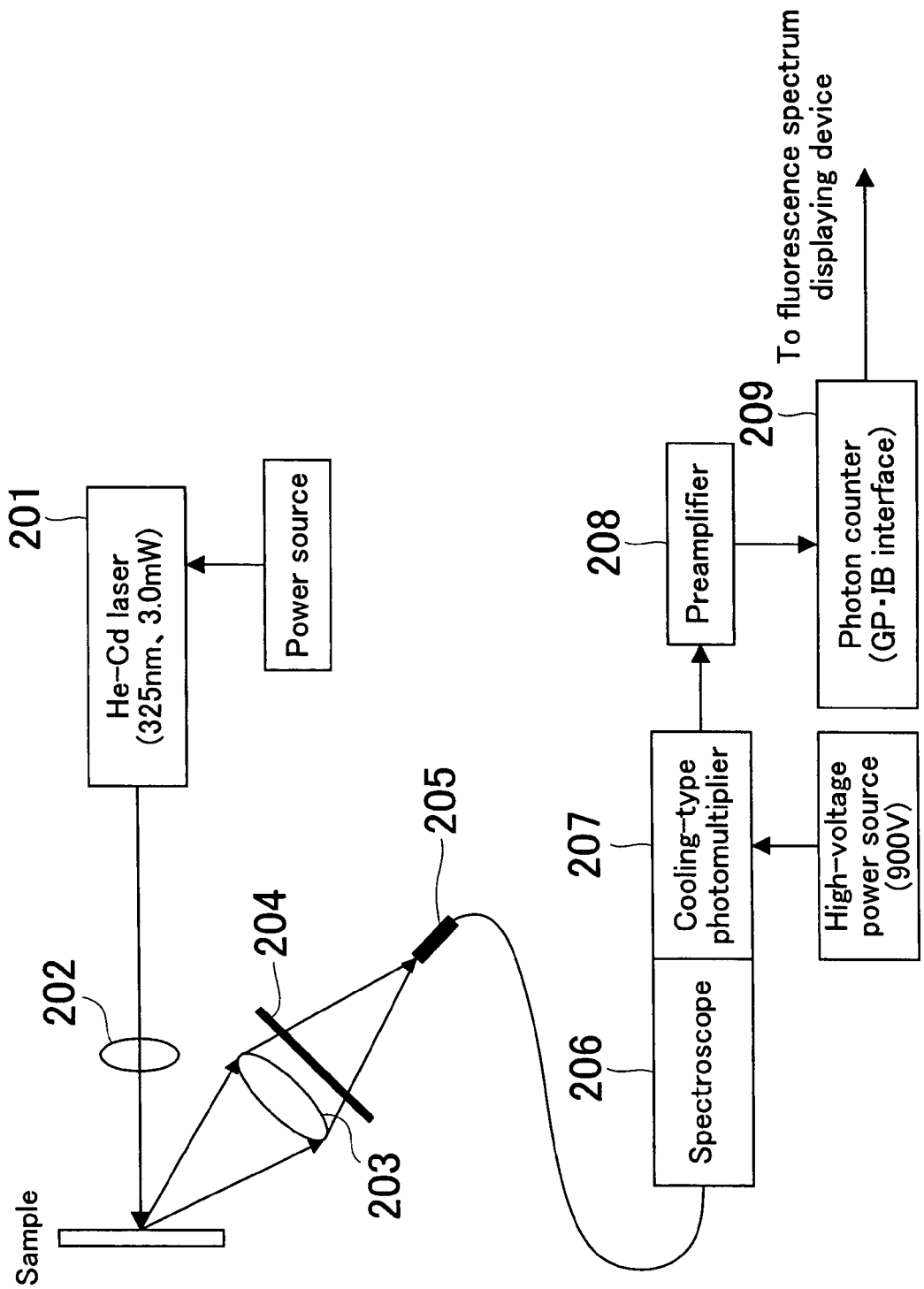
FIG. 20 is a schematic view showing the hard ware structure of the detecting device used in Embodiment 2.

The outline of the detecting device used in this measurement is shown in FIG. 20.

In FIG. 20, the exciting light form the He—Cd laser 201 is condensed by the lens 202 on the sample. The light emission from the sample is transmitted through the lens 203 and the filter 204 and then inputted into the optical fiber 205 to be led to the spectroscope 206.

The incident light introduced through the entrance slit of the spectroscope 206 is wavelength-swept in accordance with the revolution of the diffraction grating, and then the spectroscopy from the exit slit is introduced to the photomultiplier 207.

In the photomultiplier 207, the incident light is converted into electron and amplified, and then outputted as electro signal pulses. The pulses are further amplified in the preamplifier 208, and the number of pulses are counted by the photo counter 209. The measured value is data-transferred to the fluorescence spectrum displaying device (e.g., personal computer) via the GP-IB interface in the photo counter 209, and then displayed as fluorescent spectrum data.

The devices used in this embodiment are shown as follows.

Pneum Kabushiki Kaisha
    He—Cd laser 3056 (325 nm, 3.0 mW)

Nippon Roper Kabushiki Kaisha
    Spectroscope SpectraPro 275 (resolution 1.5 nm)

Hamamatsu Photonics Kabushiki Kaisha
    Cooling type photomultiplier R928

Stanford Research Systems, Inc.
    Preamplifier SR445
    Photo counter SR400

Sigma Koki Kabushiki Kaisha
    Lens 1 Piano-convex quartz lens
        (Focal distance f=60 mm, Diameter φ15 mm)
    Lens 2 Plano-convex quartz lens
        (Focal distance f=100 mm, Diameter φ30 mm)

Hoya-Schott
    Filter Y47 50 mm angle (square)

As the polycarbonate resin, EUROPIRON "E2000" made by Mitsubishi Gas Chemical Company was used. Furthermore, the fluorescent substance D was increased in affinity with respect to the resin by the surface treatment using siloxane (SH1107 made by Toray Dow Corning Corp.), subjected to compound together with the resin, and then formed into a plate shape similar to the aforementioned polypropylene. Thus, the sample was prepared.

INDUSTRIAL APPLICABILITY

According to the present invention, the information presenting substance containing-material can be easily and assuredly identified by specifying the encrypted information included in the material, and therefore the invention can be applied to information presenting substance-containing material capable of easily and assuredly processing operations such as a separation of waste materials depending on categories, a tracking survey of production history of a certain product, or checking of authenticity of a certain product. It can also be applied to the identification method, the identification system and the identification device for performing the aforementioned processing operations.

The invention claimed is:

1. An information presenting substance-containing material, containing a material and an information presenting substance,
    wherein the information presenting substance is a compound including one or more ions selected from the group consisting of a transition element ion having an incomplete 3d shell, a transition element ion having an incomplete 4d shell, a transition element ion having an incomplete 5d shell and a rare-earth element ion and therefore exhibiting one or plural respective line spectrums,
    wherein the information presenting substance is associated with specific encrypted information corresponding to the one or plural line spectrums, and wherein the encrypted information is associated with the line spectrums and represented by plural digit numeric data, wherein each digit of the numeric data corresponds to an emission wavelength of one of the line spectrums, and the value of each digit is proportional to the light emitting intensity of the substance at this wavelength.

2. The information presenting substance-containing material as recited in claim 1, wherein the material contains plural types of the information presenting substances.

3. The information presenting substance-containing material as recited in claim 1, wherein the information presenting substance exhibits at least one line spectrum within a wavelength region covering from ultraviolet light to infrared light.

4. The information presenting substance-containing material as recited in claim 1, wherein the compound is an inorganic compound.

5. The information presenting substance-containing material as recited in claim 1, wherein the compound is an organic and inorganic complex compound.

6. The information presenting substance-containing material as recited in claim 1, wherein the compound is an organic compound.

7. The information presenting substance-containing material as recited in claim 1, wherein the information presenting substance is a crystal.

8. The information presenting substance-containing material as recited in claim 1, wherein the information presenting substance is an amorphous substance.

9. The information presenting substance-containing material as recited in claim 1, wherein the information presenting substance is a complex.

10. The information presenting substance-containing material as recited in claim 1, wherein the information presenting substance is a semiconductor.

11. The information presenting substance-containing material as recited in claim 1, wherein the material is a thermoplastic plastic.

12. A product having an information presenting substance-containing material, the information presenting substance-containing material containing an information presenting substance and a material selected from the group consisting of plastic, paint, ink, paper and metal,
wherein the information presenting substance is a compound including one or more ions selected from the group consisting of a transition element ion having an incomplete 3d shell, a transition element ion having an incomplete 4d shell, a transition element ion having an incomplete 5d shell and a rare-earth element ion and therefore exhibiting one or plural respective line spectrums,
wherein the information presenting substance is associated with specific encrypted information corresponding to the one or plural line spectrums,
wherein the specific encrypted information is encrypted information regarding the product, and
wherein the encrypted information is associated with the line spectrums and represented by plural digit numeric data, wherein each digit of the numeric data corresponds to an emission wavelength of one of the line spectrums, and the value of each digit is proportional to the light emitting intensity of the substance at this wavelength.

13. A method for identifying information presenting substance-containing material, wherein the information presenting substance is a compound including one or more ions selected from the group consisting of a transition element ion having an incomplete 3d shell, a transition element ion having an incomplete 4d shell, a transition element ion having an incomplete 5d shell and a rare-earth element ion and therefore giving one or plural respective line spectrums, and wherein the information presenting substance is associated with specific encrypted information corresponding to the one or plural line spectrums, the method, comprising the steps of:
storing the line spectrums and the encrypted information in an associated manner in a storing means;
detecting the line spectrums of the information presenting substance by irradiating electromagnetic waves within a certain wavelength region against the information presenting substance-containing material or a product using the material; and
identifying the information presenting substance-containing material by specifying corresponding encrypted information based on the detected line spectrums,
wherein the encrypted information is associated with the line spectrums and represented by plural digit numeric data, wherein each digit of the numeric data corresponds to an emission wavelength of one of the line spectrums, and the value of each digit is proportional to the light emitting intensity of the substance at this wavelength.

14. An information presenting substance-containing material identification system for identifying the information presenting substance-containing material, wherein the information presenting substance is a compound including one or more ions selected from the group consisting of a transition element ion having an incomplete 3d shell, a transition element ion having an incomplete 4d shell, a transition element ion having an incomplete 5d shell and a rare-earth element ion and therefore exhibiting one or plural respective line spectrums, and wherein the information presenting substance is associated with specific encrypted information corresponding to the one or plural line spectrums, the system comprising:
a storing means which stores the line spectrums and the encrypted information in an associated manner in a storing means;
a detecting means which detects the line spectrums of the information presenting substance by irradiating electromagnetic waves within a certain wavelength region against the information presenting substance-containing material or a product in which the material is used; and
an identifying means which identifies the material by specifying corresponding encrypted information from the storing means based on the line spectrums detected by the detecting means,
wherein the encrypted information is associated with the line spectrums and represented by plural digit numeric data, wherein each digit of the numeric data corresponds to an emission wavelength of one of the line spectrums, and the value of each digit is proportional to the light emitting intensity of the substance at this wavelength.

15. An identification device for use in an information presenting substance-containing material identification system for identifying the information presenting substance-containing material, wherein the information presenting substance is a compound including one or more ions selected from the group consisting of a transition element ion having an incomplete 3d shell, a transition element ion having an incomplete 4d shell, a transition element ion having an incomplete 5d shell and a rare-earth element ion, and therefore exhibiting one or plural respective line spectrums, and wherein the information presenting substance is associated with specific encrypted information corresponding to the one or plural line spectrums, the device, comprising:

a storing means which stores the line spectrums and the encrypted information in an associated manner; and an identifying means which identifies the material by specifying corresponding encrypted information from the storing means based on the line spectrums detected by a detecting means for detecting the line spectrums of the information presenting substance by irradiated electromagnetic waves within a certain wavelength region against the information presenting substance-containing material or a product using the material, wherein the encrypted information is associated with the line spectrums and represented by plural digit numeric data, wherein each digit of the numeric data corresponds to an emission wavelength of one of the line spectrums, and the value of each digit is proportional to the light emitting intensity of the substance at this wavelength.

16. The product as recited in claim 12, wherein the material is a thermoplastic plastic.

* * * * *